United States Patent [19]

Teller et al.

[11] 4,094,979
[45] June 13, 1978

[54] ORALLY ACTIVE CEPHALOSPORINS

[75] Inventors: Daniel M. Teller, Devon; John H. Sellstedt, Pottstown, both of Pa.

[73] Assignee: American Home Products Corporation, New York, N.Y.

[21] Appl. No.: 726,709

[22] Filed: Sep. 24, 1976

[51] Int. Cl.² .................. C07D 501/36; A61K 31/545
[52] U.S. Cl. ..................................... 424/246; 544/27; 544/30
[58] Field of Search ..................... 260/243 C; 424/246

[56] References Cited

U.S. PATENT DOCUMENTS

| | | | |
|---|---|---|---|
| 3,929,781 | 12/1975 | Teller et al. | 260/243 C |
| 3,944,580 | 3/1976 | Teller et al. | 260/243 C |
| 3,947,414 | 3/1976 | Tensmeyer | 260/243 C |

*Primary Examiner*—Nicholas S. Rizzo

*Attorney, Agent, or Firm*—Richard K. Jackson

[57] ABSTRACT

Orally active, antibacterial cephalosporin derivatives of the formula:

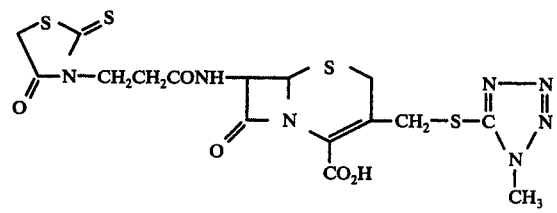

or a pharmaceutically acceptable salt thereof, compositions containing them and the process of using them are described.

7 Claims, No Drawings

ORALLY ACTIVE CEPHALOSPORINS

BACKGROUND OF THE INVENTION

U.S. Pat. No. 3,929,781, granted to applicants on Dec. 30, 1975 discloses a genus of penicillin and cephalosporin derivatives of the formula:

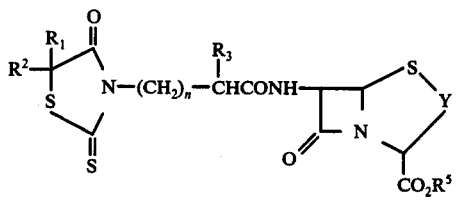

in which
R$^1$ is —H, alkyl of 1 to 6 carbon atoms, aryl of 6 to 10 carbon atoms, or aralkyl of 7 to 12 carbon atoms;
R$^2$ is —H or alkyl of 1 to 6 carbon atoms;
R$^3$ is —H, alkyl of 1 to 6 carbon atoms, monocyclic aryl of 6 to 10 carbon atoms, monocyclic aralkyl of 7 to 10 carbon atoms, —OH, —NH$_2$ or —CO$_2$H;
Y is

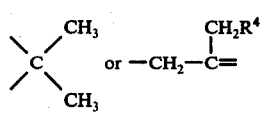

wherein R$^4$ is H, (lower) alkanoyloxy,

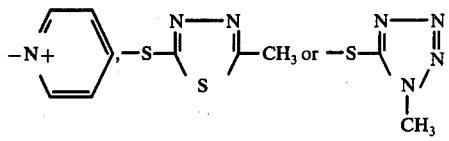

R$^5$ is —H, an alkali metal cation or the ammonium ion and
n is an integer from 0 to 5, inclusive.

The subject matter of U.S. Pat. No. 3,929,781 was made the subject of a patent application filed in Japan in July 9, 1974 as Ser. No. 79041/1974 which was published Apr. 16, 1975, and in Great Britain filed on July 23, 1974, published June 30, 1976 as Ser. No. 1,441,345.

DESCRIPTION OF THE INVENTION

In accordance with this invention, there is provided orally active, antibacterial cephalosporin derivatives of the formula:

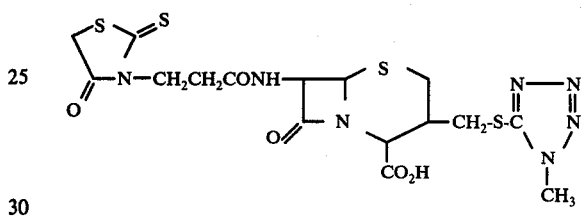

or a pharmaceutically acceptable salt thereof.

The pharmaceutically acceptable salts of the free acids of this invention are the sodium, potassium, ammonium, dicyclohexylammonium salts, and the like.

The compounds of this invention are prepared by either of the following two general procedures:

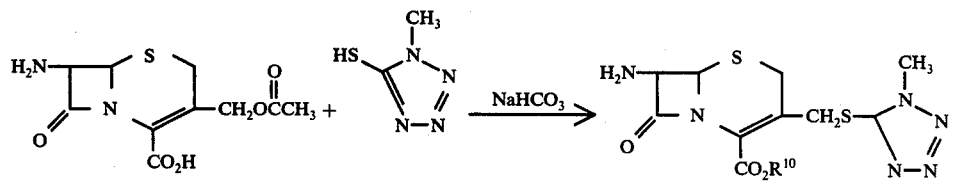

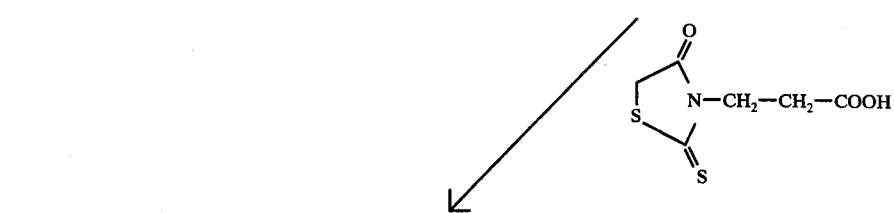

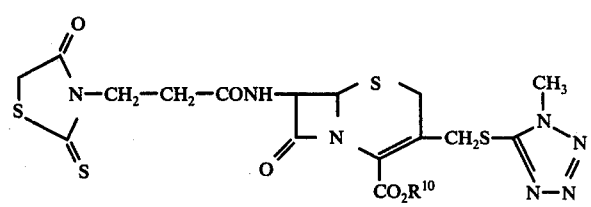

and

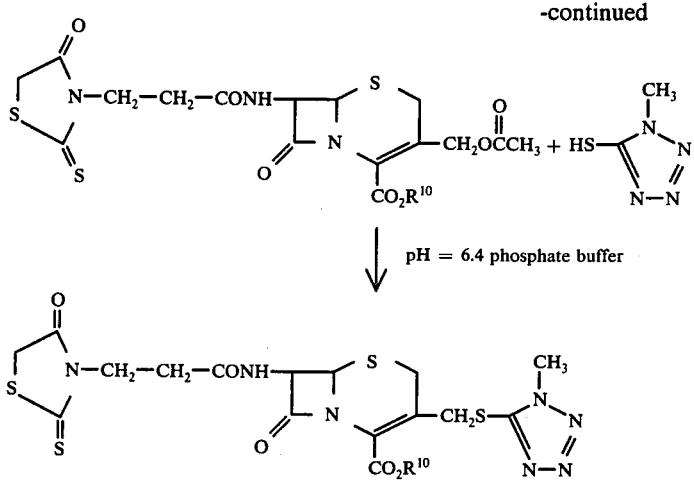

pH = 6.4 phosphate buffer

The following reference pertains to the thiol displacement: R. M. De Marinis, et al., *Journal of Antibiotics*, 28, 463 (1975). The common condensing agents for reacting the side-chain acid are isobutyl chloroformate, dicyclohexylcarbodiimide (DCC), N-hydroxysuccinimide and carbonyl diimidazole. The following referernces pertain to the side-chain acid condensation; R. G. Micetich, et al., *J. Med. Chem.*, 9, 746 (1966); U.S. Pat. No. 3,338,896. The carboxyl group of the cephalosporin may be protected, e.g., by $R^{10}$ as the t-butyl ester and later reconverted to the free carboxyl with trifluoroacetic acid [R. M. De Marinis, et al., *Journal of Antibiotics*, 28, 463 (1975)]. The side-chain acid can be prepared by the following method:

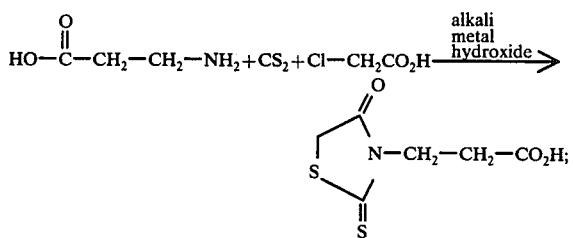

(Zuber and Sorkin, *Helv. Chim. Acta.*, 35, 1744 (1952).

The preparation of I is described in U.S. Pat. No. 3,929,781 issued Dec. 30, 1975. The displacement of the 3-acetoxy group by a thioheterocycle is described in U.S. Pat. No. 3,516,997 issued June 23, 1970 to T. Takano, et al.

EXAMPLE I

3-[(1-Methyl-1H-tetrazol-5-ylthio)methyl]-8-oxo-7-[[1-oxo-3-(4-oxo-2-thioxo-3-thiazolidinyl)propyl]amino-5-thia-1-azabicyclo[4.2.0]oct-2-ene-2-carboxylic acid A solution of 4-oxo-2-thioxo-3-thiazolidinepropionic acid (1.69 g, 0.00825 moles) in dry tetrahydrofuran (32 ml.) containing triethylamine (1.16 ml.) is cooled to −10° C. Isobutyl chloroformate (1.09 ml.) is added all at once under nitrogen and the mixture stirred at −10° C. under nitrogen for 30 minutes. A solution of 7-amino-3-[(1-methyl-1H-tetrazol-4-ylthio]-8-oxo-5-thia-1-azabicyclo[4.2.0]oct-2-ene-2-carboxylic acid (2.69 g., 0.00825 moles) in tetrahydrofuran/water (1:1, 32 ml.) containing N,N-diisopropylethylamine (1.44 ml.) is cooled to 0° C. and added rapidly to the above mixture. The temperature of the mixture is maintained at 5° C. for one hour and then 20° C. for 1 hour. The tetrahydrofuran is evaporated in vacuo <40° C. A mixture of water (300 ml.) and ethyl acetate (80 ml.) is added to the residue, the mixture shaken thoroughly and the organic layer discarded. Ethyl acetate (400 ml.) is added to the aqueous layer, the mixture cooled to 5° C. and acidified to pH 2.0 with concentrated hydrochloric acid. The organic layer is separated, washed with brine, dried over anhydrous sodium sulfate and evaporated in vacuo <40° C. The solid residue is triturated with 50 ml. of diethyl ether and filtered to give the title compound, 3.30 g. yellow solid, mp. 100°–140° C. (d); $\lambda_{max}^{KBr}$ 5.62, 5.80 μ; NMR has 1.99, 3.95 and 4.28 ppm singlets.

Anal. Calcd. for $C_{16}H_{17}N_7O_5S_4 \cdot \frac{1}{2}CH_3CH_2OCH_2CH_3$: C, 39.12; H, 4.01; N, 17.74; S, 23.22. Found: D, 39,18; H, 3.91; N, 17.58; S, 21.67.

The sodium salt of the above compound is prepared by dissolving the compound (0.50 g., 0.92 mmoles) in acetone (5.0 ml.) and adding sodium-2-ethylhexanoate (50/50 w/w in n-butanol (0.377 ml., 0.92 mmoles) at 5° C. The mixture is stirred 30 minutes at 5° C., filtered and the precipitate washed thoroughly with diethyl ether to give the sodium salt, 0.33 g. light pink solid, mp. 192°–220° C. (d); $\lambda_{max}^{KBr}$ 5.70 μ; NMR has 4.18 ppm singlet.

Anal. Calcd. for $C_{16}H_{16}N_7O_5S_4Na \cdot H_2O$: C, 34.58; H, 3.27; N, 17.64; S, 23.09; $H_2O$, 3.24. Found: C, 35.23; H, 3.13; N, 17.48; S, 20.80; $H_2O$, 3.65.

Using the same method and scale as described above for the preparation of the sodium salt, the potassium salt is prepared using 2 M potassium-2-ethylhexanoate in n-butanol (0.46 ml., 0.92 mmoles). Yield 0.42 g. light pink solid, mp. 155°–180° C. (d); $\lambda_{max}^{KBr}$ 2.90, 5.68–5.80 μ; NMR has 4.08 ppm singlet.

Anal. Calcd. for $C_{16}H_{16}N_7O_5S_4Na \cdot H_2O$: C, 34.58; H, 3.18; N, 17.15; S, 22.43; $H_2O$, 3.16. Found: C, 33.51; H, 2.84; N, 16.50; S, 20.14 $H_2O$, 4.29.

Using the same method and scale as described above for the preparation of the sodium salt, the dicyclohexylamine salt was prepared using dicyclohexylamine (0.183 ml., 0.92 mmoles). Yield 0.55 g. light pink solid, m.. 160°–170° C. (d); $\mu_{max}^{KBr}$ 3.41, 3.51, 5.60–5.80 μ; NMR has 3.86 pmm singlet.

Anal. Calcd. for $C_{28}H_{40}N_8O_5S_4$: C, 48.25; H, 5.78; N, 16.10; S, 18.40. Found: C, 48.29; H, 5.92; N, 15.68; S, 17.57.

The free acid product of Example 1 demonstrated in vitro antibacterial activity when tested by the well-known, scientifically accepted agar serial dilution procedure as follows:

| Organism | Strain No. | MIC (μg/ml) Example 1 acid |
|---|---|---|
| Ba Su | 663 | 0.97 |
| St Au | 6538P | 1.95 |
| St Au | Smith | 1.95 |
| St Au | CHP | 7.81 |
| St Au | 53-180 | 3.90 |
| My Sm | 10143 | 250 |
| Ne Ca | 819 | 31.3 |
| Ps Ae | 10145 | 250 |
| Es Co | 9637 | 3.90 |
| Es In | 65-1 | 62.5 |
| Sa Pa | 11737 | 0.97 |
| En Ae | 13048 | 250 |
| Kl Pn | 10031 | 3.90 |
| Bo Br | 4617 | 7.81 |
| Pr Vu | 6896 | 3.90 |
| He Pe | 9955 | 250 |
| Pr Mi | 9921 | 0.97 |

The oral antibacterial activity of the compounds of this invention was establihsed by intraperitoneally infecting four groups of 10 male mice CD-1 strain weighing 17-19 grams with 0.5 milliliter of a standardized suspension of bacterium in 5 percent gastric mucin. The animals were then randomized and at 6 hours post infection a single dose of the antibacterial compound being tested was given orally at 7.2, 3.6, 1.8 and 0.9 mg/mouse to each group of 10 mice. The animals were observed for 14 days and deaths were recorded daily. From this data the $CD_{50}$ (curative dose of 50 percent of the animals) was calculated.

Testing against *E. Coli* (920-$LD_{95}$), as a general representative of gram-negative bacteria, was followed by testing against *Proteus vulgaris* (347) as an example of a special application against a gram negative bacterium. In the oral anti-bacterial activity test, an arbitrary maximum dose is set at 7.2 milligrams per mouse below which activity must be found before a compound is considered orally active. The arbitrary maximum dose of 7.2 milligrams per mouse represents a practical dose limit in terms of the potency of known orally active antibacterial agents.

The sodium salt of the product of Example 1 demonstrated oral antibacterial activity in comparison to Cephradine® as follows:

| Cephalosporin | Route | E. Coli | $CD_{50}$ (mg/mouse) | | | | St Au (Smith) |
|---|---|---|---|---|---|---|---|
| | | | Pr Bu | Pr Mi | Kl Pn | St Py | |
| Ex. 1- Na salt | P.O. | 2.35 | 5.97 | 4.49 | 1.36 | >3.6 | 2.73 |
| Cephradine | P.O. | 2.27 | 6.52 | 2.25 | 2.42 | <0.45 | 0.140 |

The potassium salt of the product of Example 1 afforded a $CD_{50}$ of 3.05 mg/mouse against *E. Coli* (920); (E-2) 3.30 mg/mouse; (E-3) 2.12 mg/mouse; 5.90 against *Pr vulgaris* (347); although it was inactive against *E. Coli* W-102 at 7.2 mg/mouse.

The free acid, buffered to pH 4.9 in aqueous solution, afforded a $CD_{50}$ of 2.97 mg/mouse against *E. Coli* (920), 5.97 mg/mouse against *Pr vulgaris* (Pr-347), and 2.73 mg/mouse against St Au (Smith).

Cephalosporins which are known to have oral activity usually contain an alpha-amnio group on the 7-acylamido side chain, which acylamido side chain heretofore was limited to the 7-acetamido side chain or a modification thereof. The compounds of this invention represent the first known instance of oral activity of a cephalosporin derivative containing a 7-propionamido side chain lacking an alpha-amino group.

Furthermore, the oral activity of the compounds of this invention is surprising when it is considered that each of the compounds depicted in the following structural formula were found inactive at the maximum oral dose of 7.2 mg./mouse:

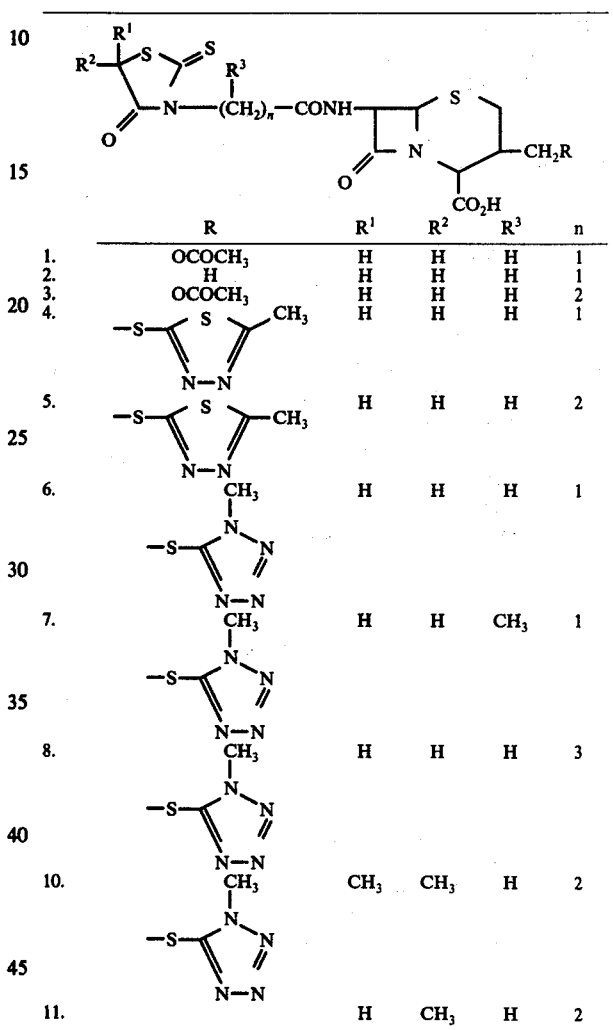

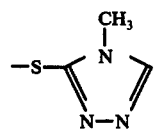

The antibacterial agents of this invention are administered to a warm blooded animal suffering from a bacterial infection either parenterally or orally. The dose to be administered is determined by the physician as with other known cephalosporin antibacteral agents, based upon the severity of the condition under treatment and the size, age and other general physical characteristics of the given patient. Oral administration is vastly preferred because of the ease involved in self administration by the patient.

The compounds of this invention may be formulated for oral administration into tablets, capsules or suspensions in which they are combined with conventionaly used diluents or excipients. Thus, a typical composition for tablets would contain a unit dose of one of the cephalosporin derivatives of this invention with a diluent such as lactose, sorbitol, mannitol, etc., a lubricant such as magnesium or calcium stearate, a polyethyleneglycol, etc., a binder such as sodium carboxymethyl cellulose, corn starch, etc., and, if desired, a sweetener or flavor. Typical capsule formulations contain the cephalosporin of this invention in unit dosage form (ca. 250 mg.); Cab-o-Sil M-5 (ca. 15.0 mg); magnesium stearate, U.S.P. (ca. 20.0 mg.); and lactose, U.S.P. (ca. 250.0 mg.). It is well within the skill of the art to vary the formulations for administering the antibacterial agents disclosed herein.

For parenteral administration i.v. or i.m., sterile aqueous solutions buffered to about pH 4.9 to about 7 are suitable for direct use and storage of the free acid, while the salts may be employed without a buffer. Conventional excipients including stabilizers, suspending agents and buffering agents may be employed as desired.

What is claimed is:
1. A compound of the formula:

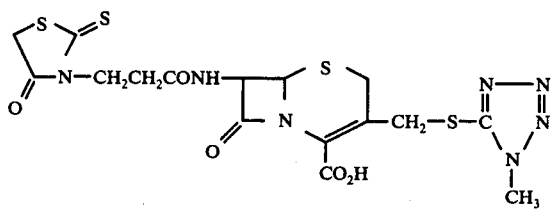

or a pharmaceutically acceptable salt thereof.

2. A compound of claim 1 which is 3-[(1-methyl-1H-tetrazol-5-ylthio)methyl]-8-oxo-7-[(1-oxo-3-(4-oxo-2-thioxo-3-thiazolidinyl)propyl]amino-5-thia-1-azabicyclo[4.2.0]oct-2-ene-2-carboxylic acid sodium salt.

3. A compound of claim 1 which is 3-[(1-methyl-1H-tetrazol-5-ylthio)methyl]-8-oxo-7-[(1-oxo-3-(4-oxo-2-thioxo-3-thiazolidinyl)propyl]amino-5-thia-1-azabicyclo[4.2.0]oct-2-ene-2-carboxylic acid potassium salt.

4. A compound of claim 1 which is 3-[(1-methyl-1H-tetrazol-5-ylthio)methyl]-8-oxo-7-[(1-oxo-3-(4-oxo-2-thioxo-3-thiazolidinyl)propyl]amino-5-thia-1-azabicyclo[4.2.0]oct-2-ene-2-carboxylic acid ammonium salt.

5. A compound of claim 1 which is 3-[1-methyl-1H-tetrazol-5-ylthio)methyl]-8-oxo-7-[(1-oxo-3-(4-oxo-2-thioxo-3-thiazolidinyl)propyl]amino-5-thia-1-azabicyclo[4.2.0]oct-2-ene-2-carboxylic acid dicyclohexylamine salt.

6. A method for treating bacterial infections in a warm blooded animal which comprises orally administering to said animal an antibacterially effective amount of a compound of the formula:

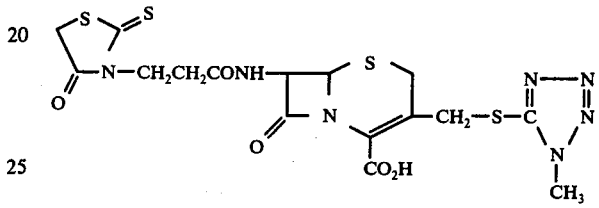

or a pharmaceutically acceptable salt thereof.

7. A pharmaceutical composition for oral administration comprising an antibacterial amount of a compound of the formula:

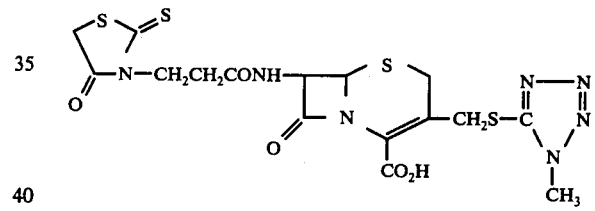

or a pharmaceutically acceptable salt thereof and a pharmaceutically acceptable non-toxic diluent therefor.

* * * * *